US00PP12173P2

(12) United States Plant Patent
Swartz et al.

(10) Patent No.: US PP12,173 P2
(45) Date of Patent: Oct. 30, 2001

(54) RASPBERRY PLANT NAMED 'JOSEPHINE'

(75) Inventors: Harry Jan Swartz, Laurel, MD (US); Joseph A. Fiola, Whiting, NJ (US); Herbert D. Stiles, Blackstone, VA (US); Brian R. Smith, River Falls, WI (US)

(73) Assignees: University of Maryland, College Park, MD (US); Virginia Tech Intellectual Properties, Inc., Blacksburg, VA (US); University of Wisconsin at River Falls, River Falls, WI (US)

( * ) Notice: Subject to any disclaimer, the term of this patent is extended or adjusted under 35 U.S.C. 154(b) by 0 days.

(21) Appl. No.: 09/177,127

(22) Filed: Oct. 22, 1998

(51) Int. Cl.[7] ..... A01H 5/00
(52) U.S. Cl. ..... Plt./204
(58) Field of Search ..... Plt./204

(56) References Cited

U.S. PATENT DOCUMENTS

P.P. 653 * 3/1945 Drain ..... Plt./204
P.P. 5,404 * 2/1985 Sanford et al. ..... Plt./204
P.P. 10,610 * 9/1998 Swartz et al. ..... Plt./204

* cited by examiner

*Primary Examiner*—Bruce R. Campell
*Assistant Examiner*—Wendy C Baker

(57) ABSTRACT

The present invention is a new and distinct fall bearing red raspberry cultivar named 'Josephine', which is capable of producing fruit on primocanes, the fruit being larger, with tougher skin and more cohesive than that of the standard cultivars. The cultivar is characterized by moderate suckering ability and its large, round and extremely symmetrical fruit which ripens later than standard cultivars. Most drupelets tear apart rather than separate from each other and it is common to observe perfectly curvilinear rows of drupelets, i.e. along the latitudinal circumference of the fruit.

5 Drawing Sheets

FIELD OF THE INVENTION

This invention concerns a new and distinct cultivar of raspberry plant with a botanical name of *Rubus ideaus L.*

DESCRIPTION OF RELATED PRIOR ART

Several cultivars of raspberry plant are known. For instance, raspberry cultivars named 'Anne', 'Caroline' and 'Lauren' have been described in U.S. Plant Pat. No. 10,411, 10,412 and 10,610, respectively. The new and distinct cultivar of the present invention is a raspberry plant named 'Josephine'. This new and distinct cultivar of the present invention differs from 'Anne' in bearing red fruit, while 'Anne' bears golden fruit. Compared with 'Anne', 'Josephine' also has simpler leaf serration, produces more root- and crown-suckers and has a later ripeness period for the fruit, which is usually more free from rot in the field. 'Josephine' can be distinguished from 'Caroline' in that 'Josephine' yields a lower proportion of cane producing fruit and has a later ripeness period for the fruit, which is larger and has less fruit rot and late season rust. 'Josehphine' leaves do not regularly curl in high sun and warm temperatures as 'Caroline'. 'Josephine' and 'Lauren' are both red raspberry cultivars, but 'Josephine' can be distinguished from 'Lauren' in that 'Josephine' is fall bearing, while 'Lauren' is spring bearing.

ORIGIN OF THE NEW CULTIVAR

The new cultivar of fall bearing red raspberry originated from a controlled cross at the University of Maryland Greenhouses in College Park, Md. The cross "EF" was 'Amity' (unpatented)×'Glen Gerry' (unpatented) and was made in the winter of 1989. This year was designated "J" as part of the University of Maryland at College Park; Rutgers University of New Brunswick, N.J.; Virginia Polytechnic Institute and State University, Southern Piedmont Agricultural Research and Education Center at Blackstone; and the University of Wisconsin at River Falls cooperative breeding program. The clone was first selected in 1992 at the Rutgers Cream Ridge Fruit Agricultural Experiment Station and was therefore designated "-f1". Thus, the complete breeding designation was "JEF-f1". JEF-b1, a sister seedling named 'Anne', disclosed in U.S. Plant Pat. No. 10,411, was selected a year earlier in Blackstone, Va.

SUMMARY OF THE NEW CULTIVAR

This application relates to a new and distinct red fruited, fall bearing raspberry cultivar, botanically known as *Rubus ideaus L.* The following characteristics are outstanding:

1. Production of fruit on primocanes which is much more cohesive than the standard cultivars in use and equal to that of all but one of the new cultivars available for trial; 'Autumn Britton' (unpatented).
2. In all the areas of test of this selection, the fruit is larger than all cultivars known to us, except its sister seedling 'Anne' (U.S. Plant Pat. No. 10,411) and 'Ruby', a cultivar from New York. The fruit is later than 'Anne' and has a different color. It is much firmer and cohesive than 'Ruby' (syn. 'Watson' U.S. Plant Pat. No. 7,067).
3. It is productive, but later in the season than all of the cultivars known to us to be presently in use. This characteristic makes it suitable for completing the season in California, the Mid-Atlantic States and in the southern Mid-West. As this cultivar was tested as a primocane bearer, meaning all overwintering canes were removed, no claim is made regarding its cold hardiness or chilling requirement.

The following characteristics are useful in distinguishing this cultivar from other cultivars and can be useful for cultivar identification.

1. Plants are modeately suckering (about 65–70 sucker plants per 10 foot of row) and very upright, producing about three quarters as many canes as 'Heritage' (unpatented) and growing to 4 feet or taller when mature.

2. The fruit is round conic with a cavity about 40% of the fruit diameter, very cohesive, red and very symmetrical. Drupelets will often tear in half before separating from the neighboring drupelets.

3. The fruit has an even collar and has a noticeable amount of pubescence when ripe.

4. Primocanes are light green (Royal Horticultural Society plate 145A) with a red blush (Royal Horticulural Society plate 183A) and only a moderate amount of characteristic stout red colored (Royal Horticultural Society plate 183A) thorns per node. Fruit is typicallly 2–3 weeks later to initate ripening than 'Caroline' (U.S. Plant Pat. No. 10,412), 'Heritage' (unpatented) and 'Autumn Britton' (unpatented), new standards for fall production in the United States. Fruit will appear on the upper quarter of the cane.

5. The cultivar may be distinguished from its sister, 'Anne' (U.S. Plant Pat. No. 10,411), by its red fruit and thorns and simpler leaf serration.

BRIEF DESCRIPTION OF THE PHOTOGRAPHS

The accompanying photographs show typical characteristics of the new variety:

Figure 3:
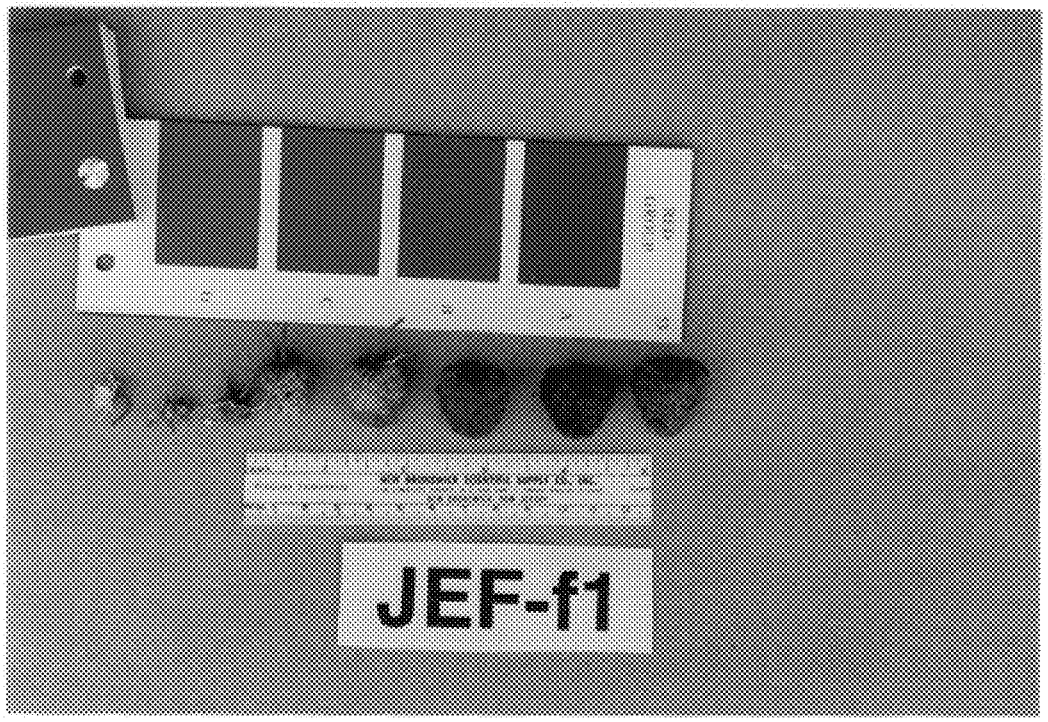

FIG. 3. shows development of 'Josephine' flowers and fruit and The Royal Horitultural Society color plates 53 A through D (A on left).

Figure 4:
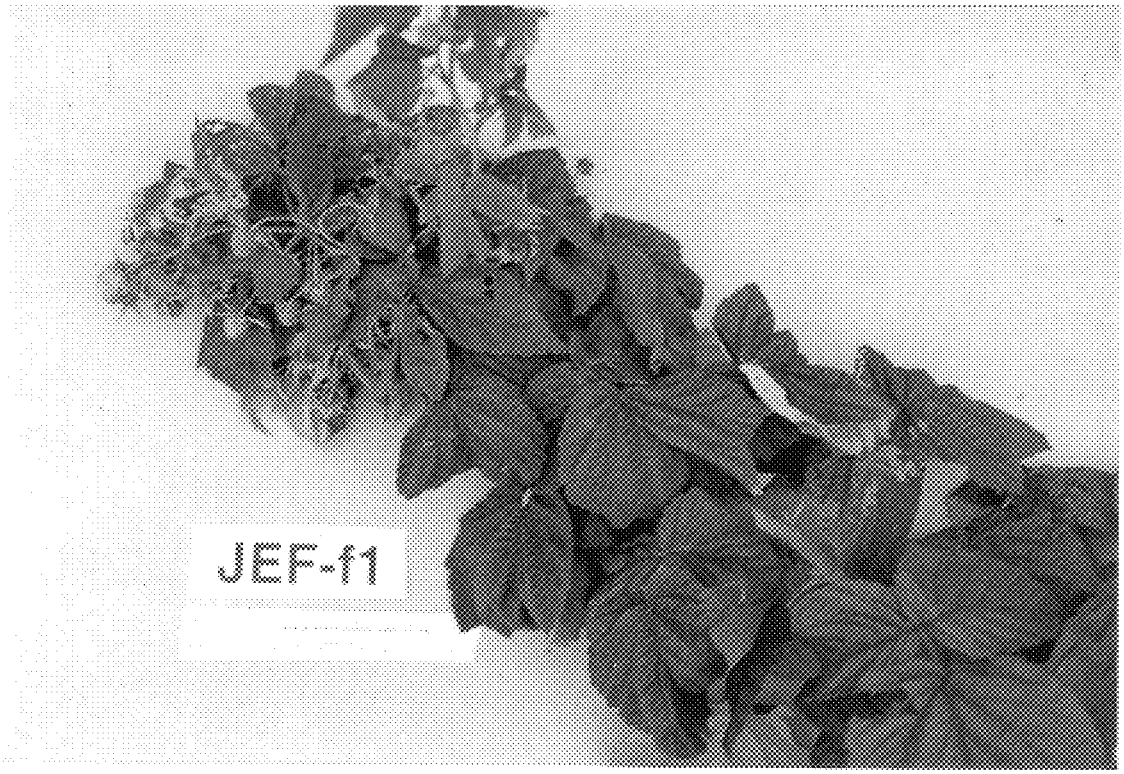

FIG. 4 shows a fruiting cluster of 'Josephine', showing the exposure of 'Josephine' fruit.

Figure 5:
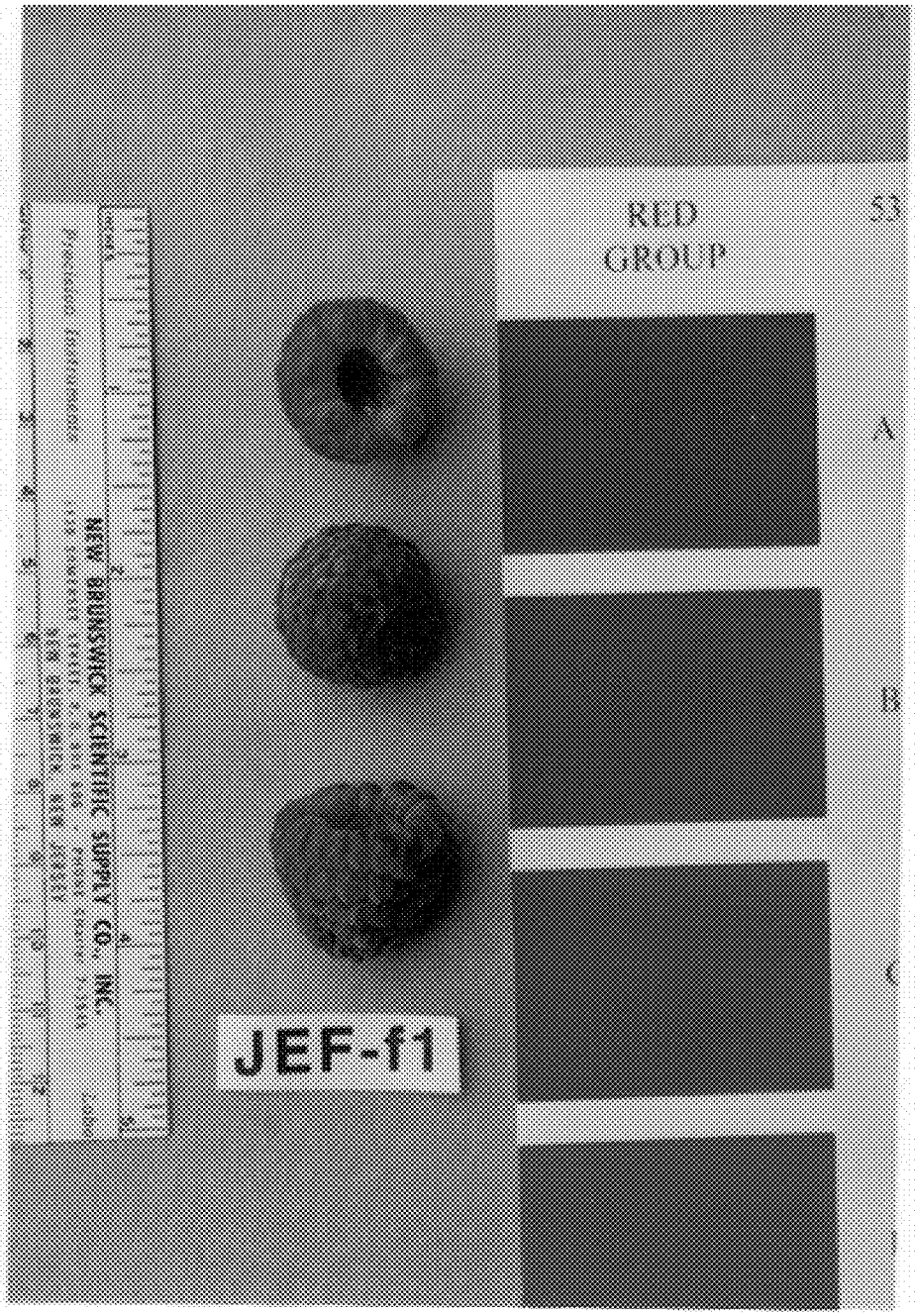

FIG. 5 shows the size, pubescence and uniformity of harvested 'Josephine' fruit and The Royal Horticultural Society color plates 53 A through D.

DESCRIPTION OF THE NEW CULTIVAR

The following is a detailed description of the new cultivar, including fruit production, together with the cultivar's morphological characteristics. The characteristics of the cultivar were compared with other standards used in the Mid-Atlantic Region of the U.S. The description is based on information provided by cooperating scientists from plants grown in fields at Cream Ridge N.J., Colt's Neck, N.J., Millersville, Pa., S. Deerfield, Mass., and from plants grown in the greenhouses at College Park, Md.

Figure 1:
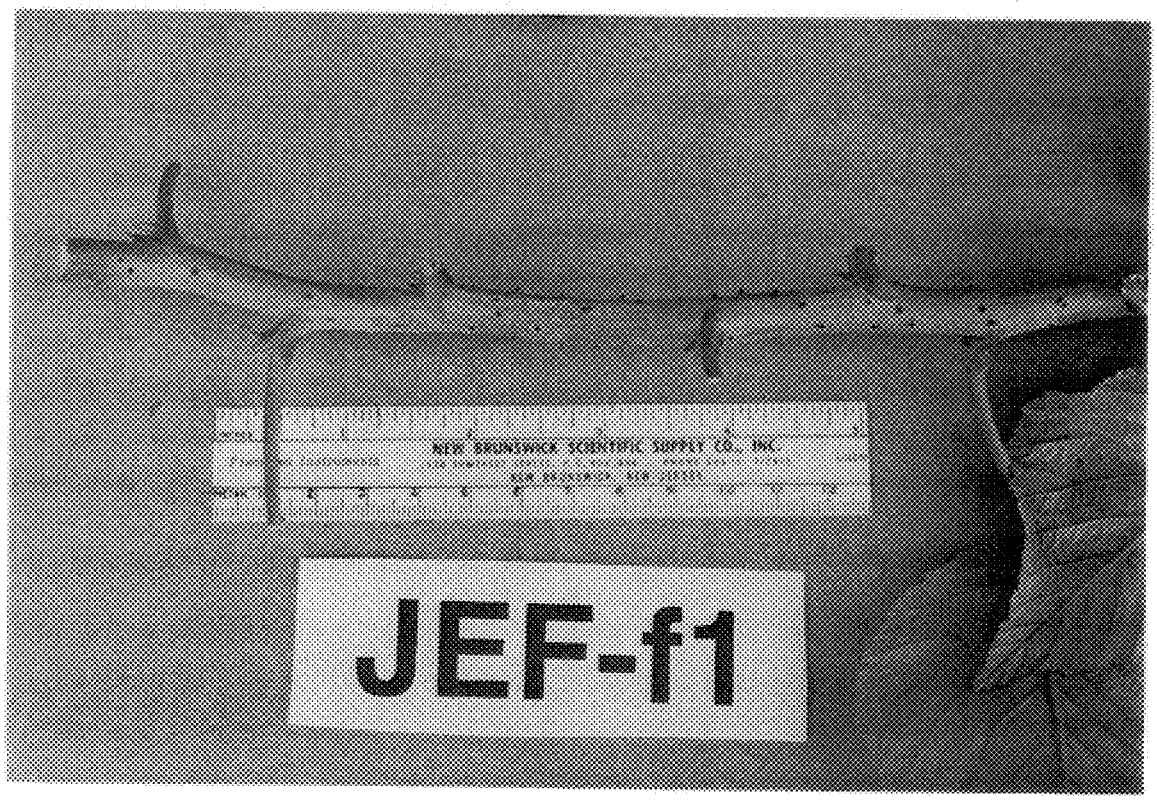
FIG. 1 shows the density of thorns on a 'Josephine' primocane.
Figure 2:
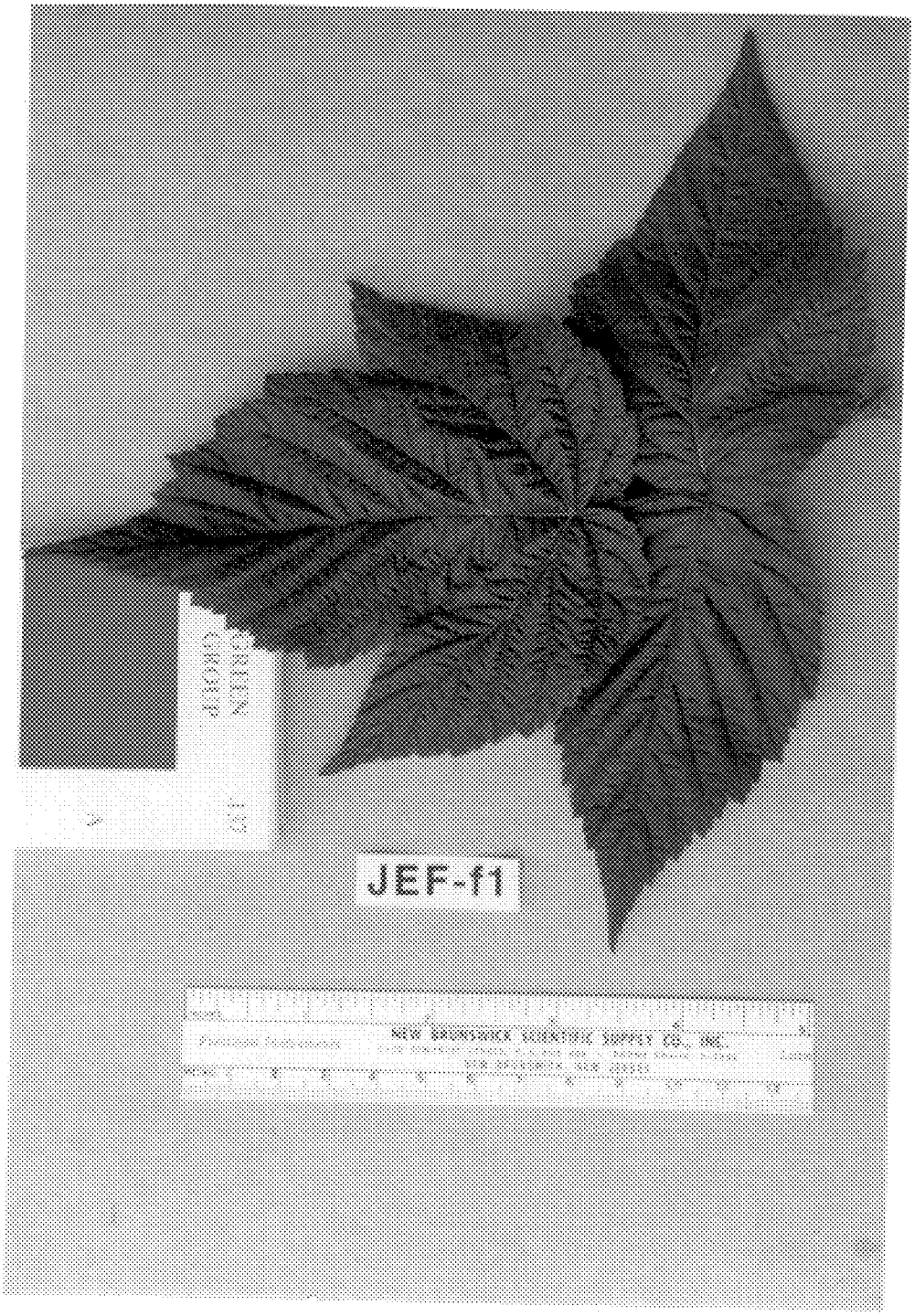
FIG. 2 shows a 'Josephine' leaf, with simpler serration than 'Anne' and a Royal Horticultural Society 137A number color plate.

'Josephine' produces a moderate number of rot- and crown-suckers (approximately 65–70 per 10 foot of row, from 3 year old plants grown in Colt's Neck, N.J.), more than 'Anne', similar to 'Caroline' but less than 'Heritage'. During the growing season, primocanes are light green colored (Royal Horticultural Society plate 145A) with a purple blush (Royal Horticultural Society plate 183A) in full sun, usually unbranched, erect and moderately vigorous. Floricanes are moderately exfoliating at their base, but with unbroken epidermis at their apex. Floricane color is light brown throughout (Royal Horticultural Society plate 165B). During their first growing season, thorns are moderate in density, 1 mm or less in length, stout (the diameter of the thorn at the base is half the thorn length) and purple (Royal Horticultural Society plate 183A) in color (see FIG. 1). The red coloration extends another 1 mm into the surrounding cane. The upper surface of the leaves are dark green, most closely in hue to Royal Horticultural Society Color Plate 137A and the lower surface is pubescent resembling Royal Horticultural Society plate 191C, trifoliolate to pentafoliolate and average 14 cm from the distal end of the petiole to the distal end of the terminal leaflet (see FIG. 2). Petiole color is light green (Royal Horticultural Society plate 145A) and the petioles have a moderate amount of thorns, similar to those on the cane. The basal leaflets average 20 cm from terminal point to point. Leaf serration is common for most cultivars of red raspberry and cannot be used to distinguish this cultivar.

Fruit is borne on the top of the primocanes; the proportion of cane producing fruit is similar to 'Anne' (U.S. Plant Pat. No. 10,411), 'Autumn Bliss' (U.S. Plant Pat. No. 6,597), 'Autumn Britton' (unpatented), 'Amity' (unpatented) or 'Ruby' (U.S. Plant Pat. No. 7,067), but less than 'Heritage' (unpatented), 'Caroline' (U.S. Plant Pat. No. 10,412) and 'Summit' (unpatented). Because the fruit is larger than 'Heritage' or 'Caroline' (U.S. Plant Pat. No. 10,412), yield per cane is greater on 'Josephine' canes (see Table 1). The basal three quarters of the cane can produce a crop in the next spring, but no overwintering has been attempted with this fall bearing cultivar. Canes will flower in late July to late August, depending on latitude, and fruit from early September through to the first frost in the eastern U.S. This ripeness period is 2 or more weeks later than 'Polana' (unpatented), 'Caroline' (U.S. Plant Pat. No. 10,412), 'Autumn Bliss' (U.S. Plant Pat. No. 6,597), 'Autumn Britton' (unpatented), 'Heritage' (unpatented) and 'Anne' (U.S. Plant Pat. No. 10,411). Other late ripening cultivars, like 'Ruby' (U.S. Plant Pat. No. 7,067) and 'September' (unpatented) do not closely resemble 'Josephine' as they are much less cohesive and firm. The unscented flower morphology and early fruit morphology are typical or most red raspberry cultivars, five white 0.5 cm long petals which abscise within 4 days after pollination, five 0.9 cm long sepals (Royal Horticultural Society plate 194B), 1.3 to 2.0 cm total flower diameter, and cannot be used to identify 'Josephine' (see FIG. 3). Fruit trusses are typical cymose clusters averaging 38 fruit per cane with a larger proportion of basal fruit ripening first (see FIG. 4). Flower abscission is rare, except when flowers are lost to frost or later flowers are aborted due to excessively heavy crop load. Fruit are easily distinguishable for this variety at 20 days post pollination. They are moderate red when ripe, both internally and externally, closely resembling the hue of Royal Horticultural Society color plate number 53A (see FIG. 5). Fruit have a noticeable pubescence, typical of a few other varieties, but none of the later ripening red fall bearing raspberries. Fruit is round-conic, average fruit length to width is 1.0, very large (primary fruit averages 2.5 cm in diameter) and very symmetrical. Drupelets are held together tightly. The collar is very uniform with one small notch per fruit. The cavity width is 40% of the diameter of the fruit, approximately 1.0 cm., which is a smaller proportion than most round fruited cultivars because the drupelet thickness (0.7 cm) is higher than most cultivars. This combination of traits, with the additional pubescence, partially accounts for the superior cohesiveness of 'Josephine' fruit. The fruit readily separates from the plant's recepticle, even when slightly unripe. The fruit does not break down after at least one week in common storage at 40° F. The fruit has less fruit rot and late season rust than other fall bearing cultivars ('Heritage' (unpatented), 'Autumn Bliss' (U.S. Plant Pat. No. 6,597), 'Caroline' (U.S. Plant Pat. No. 10,412) and 'Polana' (unpatented). Flavor is mild to sweet and characteristic of red raspberry. The texture of the fruit is firmer and drier than other cultivars, i.e. it is not as "juicy".

The plant is field resistant to many of the common insect pests, especially potato leaf hopper, and diseases in the eastern United States, e.g. mildew, late season yellow rust, anthracnose and verticillium wilt. The plant's reaction to *Phytophthora fragarae* root rot is probably moderately resistant, based on field reaction, not to controlled testing. Fruit is usually free from rot in the field, more so than 'Anne', 'Josephine's' sister seedling.

FRUIT PRODUCTION

'Josephine' has been tested in a replicated trial in Cream Ridge, N.J. The following data were collected in the summer and fall of 1998. Plants were planted in July 1997, the data below could be classified as an early partial yield. The summer of 1998 was characterized by normal temperatures, but below normal rainfall.

TABLE 1

Comparison of fresh fruit characteristics of 'Josephine'

| | Caroline | Heritage | Josephine |
|---|---|---|---|
| Yield in thousand of lbs/acre | 1433 | 4408 | 1669 |
| Yield in grams per cane | 70.5 | 86.7 | 101.7 |
| Fruit Weight in Grams | 2.0 | 1.5 | 2.9 |
| Percentage of Season: | | | |
| before Sept 1 | 14 | 11 | 5 |
| from Sept 1–15 | 14 | 35 | 15 |
| from Sept 16–30 | 27 | 35 | 33 |
| from Oct 1–15 | 45 | 18 | 4 |

'Josephine' was asexually reproduced from lateral bud meristems in S. Deerfield, Mass. and College Park, Md. It can also be tissue cultured or field propagated by root suckers. No off-type plants have been observed in the history of propagation of this cultivar. Tissue culture explants originated from lateral bud meristems and multiplication medium contained 3 to 15 micromolar benzyl adenine. The plant has been propagated since 1994 in S. Deerfield, Mass. and at College Park, Md.

What is claimed is:

1. A new and distinct fall bearing red raspberry plant known as 'Josephine' as described herein, illustrated and identified by the characteristics set forth above.

* * * * *